United States Patent [19]

Sano et al.

[11] Patent Number: 5,189,201

[45] Date of Patent: Feb. 23, 1993

[54] PROCESS FOR PREPARATION OF LOWER FATTY ACID ESTER

[75] Inventors: Kenichi Sano; Masaaki Nishiyama; Toshiro Suzuki; Shoichiro Wakabayashi; Kuniaki Miyahara, all of Oita, Japan

[73] Assignee: Showa Denko K.K., Tokyo, Japan

[21] Appl. No.: 857,496

[22] Filed: Mar. 25, 1992

[51] Int. Cl.$^5$ ............................................. C07C 69/52
[52] U.S. Cl. ..................................... 560/205; 560/245
[58] Field of Search ................................ 560/205, 245

[56] References Cited

U.S. PATENT DOCUMENTS

| | | | |
|---|---|---|---|
| 2,415,000 | 1/1947 | Bearse et al. | 560/205 |
| 3,539,021 | 11/1970 | Cipollone et al. | 560/205 |
| 3,894,076 | 7/1975 | Van Duyne | 560/205 |
| 4,301,298 | 11/1981 | Horlenrco et al. | 560/206 |
| 4,490,553 | 12/1984 | Chase et al. | 560/205 |
| 4,824,998 | 4/1989 | Inoue et al. | 560/205 |
| 5,138,092 | 8/1992 | Perez et al. | 560/205 |

FOREIGN PATENT DOCUMENTS

| | | |
|---|---|---|
| 268999 | 1/1988 | European Pat. Off. |
| 47-7775 | 6/1972 | Japan . |
| 7235884 | 9/1972 | Japan . |
| 47-42808 | 10/1972 | Japan . |
| 8006131 | 4/1978 | Japan . |
| 56-30334 | 7/1981 | Japan . |
| 1179356 | 1/1970 | United Kingdom . |
| 2085870 | 5/1982 | United Kingdom . |

*Primary Examiner*—Paul J. Killos
*Attorney, Agent, or Firm*—Sughrue, Mion, Zinn, Macpeak & Seas

[57] ABSTRACT

A lower fatty acid ester such as ethyl acetate or ethyl acrylate is prepared by a process in which a lower fatty acid such as acetic acid or acrylic acid is reacted with a lower olefin such as ethylene by using as solid catalyst a heteropoly-acid or its salt. The esterification is carried out in gaseous phase.

19 Claims, No Drawings

PROCESS FOR PREPARATION OF LOWER FATTY ACID ESTER

BACKGROUND OF THE INVENTION

1. Field of the Invention

The present invention relates to a process for preparation of a fatty acid ester with remarkably good productivity (hereinafter referred to as space time yield) by reacting a lower fatty acid and a lower olefin.

2. Description of the Related Art

In the past, as a process for preparation of such an ester by reaction of a lower fatty acid with a lower olefin, there has been known the process, as disclosed in Japanese Examined Patent Publication (Kokoku) No. 53-6131, of using as a catalyst sulfuric acid, phosphoric acid, or other mineral acid, phosphotungstic acid, phosphomolybdic acid, or other heteropoly-acids. Further, Japanese Examined Patent Publication (Kokoku) No. 47-42808 and Japanese Examined Patent Publication (Kokoku) No. 56-30334 disclose processes for a reaction in the liquid phase using as a catalyst phosphotungstic acid, phosphomolybdic acid, or other heteropoly-acid or an acid metal salt of phosphotungstic acid or silicotungstic acid.

In these conventional processes using a catalyst, however, the space time yield was low and the life of the catalyst was short, so the production process was far from being of industrial use.

SUMMARY OF THE INVENTION

The present invention was made in consideration of the above circumstances and has as its object the provision of a process able to easily prepare a lower fatty acid ester with a remarkably higher space time yield compared with the conventional processes and with discovery of a catalyst with a long life.

To achieve the above-mentioned object, there is provided a process for the preparation of a lower fatty acid ester wherein a lower fatty acid is reacted with a lower olefin in gaseous phase by using as a solid catalyst at least one heteropoly-acid salt selected from cesium, rubidium, thallium, ammonium, potassium, barium, gold, sodium lithium, copper and magnesium salts of phosphotungstic acid, silicotungstic acid, phosphomolybdic acid and silicomolybdic acid.

According to another aspect of the present invention, there is provided a process for the preparation of a lower fatty acid ester wherein a lower fatty acid is reacted with a lower olefin in gaseous phase by using as a solid catalyst at least one member selected from heteropoly-acids and their salts represented by the general formula,

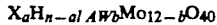
$$X_a H_{n-al\,A}W_b Mo_{12-b}O_{40}$$

wherein H W Mo and O respectively represent hydrogen, tungsten, molybdenum, and oxygen, X represents at least one element or atomic group selected from the group consisting of potassium, rubidium, thallium, cesium, and ammonium, A represents at least one element selected from the group consisting of phosphorous and silicon, a represents an atomic ratio or molecular ratio of the elements or atomic groups, b is an integer of less than 12, not including 0, n is 3 when A is phosphorous, and n is 4 when A is silicon.

DESCRIPTION OF THE PREFERRED EMBODIMENTS

As the lower fatty acid usable in the process of the present invention, mention may be made of a saturated or unsaturated fatty acid having up to four carbon atoms, for example, formic acid, acetic acid, propionic acid, valeric acid, acrylic acid, methacrylic acid, and crotonic acid. As the lower olefin, mention may be made of olefins having up to four carbon atoms, for example, ethylene, propylene, butene-1, butene-2, and isobutene.

If use is made of an olefin with five or more carbon atoms, the synthesis reaction of the fatty acid ester becomes slower. If the reaction pressure or the reaction temperature is increased to speed this up, not only do the polymers and other byproducts increase, but the catalyst life becomes remarkably shorter.

The reaction pressure preferably is 0 to 50 kg/cm$^2$G, more preferably 0 to 10 kg/cm$^2$G. The reaction temperature preferably is 50 to 300° C., more preferably 100 to 250° C. If the reaction temperature is less than 50° C., the reaction rate becomes slower and the space time yield becomes remarkably lower. Further, if it exceeds 300° C., the byproducts increase and the catalyst life becomes shorter.

The molar ratio of the lower olefin to the lower fatty acid is not critical, but the ratio is preferably 1 to 30, more preferably 3 to 20 from the view point of the reaction rate.

The reaction may preferably be carried out in the presence of water vapor from the point of view of increasing the catalyst life.

If water vapor is present in the reaction system, alcohol is synthesized. The reason is not clear, but the catalyst life becomes longer if about 1 percent by volume of water vapor is added to the material gas.

In the reaction, it is preferable to pass the material gas, under standard conditions, through the catalyst at a space velocity (SV) of 100 to 5000 hr$^{-1}$, more particularly 300 to 2000 hr$^{-1}$.

The catalyst is an acid salt of a heteropoly-acid such as phosphotungstic acid. The acid salt becomes better with a larger surface area, a certain acid strength, and a larger amount of acid.

The catalyst may be used alone or supported on a carrier. The carrier may be a porous or porous grain-forming substance generally used as a catalyst carrier, and may be of silica, diatomaceous earth, titania, activated carbon, alumina or silica-alumina, or a mixture of two or more thereof. The catalyst may be supported on the carrier by coating, impregnation, evaporation to dry or kneading and molding.

The catalyst may be prepared, for example, by dissolving commercially available phosphotungstic acid or the like in a suitable amount of water and adding and mixing into the same a nitrate or carbonate of cesium, rubidium, thallium, ammonium, potassium, or the like as is in a powder form or as an aqueous solution. The mixture is then evaporated to dryness to obtain a solid heteropoly-acid salt. The catalyst may be supported on a carrier by any methods. For example, the above-mentioned liquid mixture in a slurry or solution state is impregnated into a carrier to be supported on the carrier, or is kneaded with a carrier powder, or the heteropoly-acid salt is deposited on the carrier, for example, by coating. Then, the obtained solid material is heat treated in the air or a nitrogen or other inert gas atmosphere at 50 to 350° C., preferably 100 to 300° C. If the temperature is less than 50° C., the moisture content is not sufficiently removed, while if over 350° C., the catalyst deteriorates.

The mixed coordination heteropoly-acid catalyst used in the second process of the present invention is better when having a larger surface area, a stronger acid strength, and a larger amount of acid and may be used as is or supported on a carrier.

The carrier used may be a porous or porous grain forming substance generally used as a carrier, for example, may be silica, diatomaceous earth, titania, activated carbon, alumina, silica-alumina, etc. The catalyst may be supported on the carrier as mentioned hereinabove for the first process of the invention.

The above-mentioned mixed coordination heteropoly-acid catalyst may be prepared by, for example, dissolving commercially available phosphotungstomolybdic acid or silicotungstomolybdic acid in water and adding and mixing to the same a nitrate or carbonate of cesium, rubidium, thallium, ammonium, or potassium as is as a powder or as an aqueous solution. Next, the resultant solid is heat treated in the air or a nitrogen or other inert gas atmosphere at 50 to 350° C., preferably 100 to 300° C. If the temperature is less than 50° C., the moisture content is not sufficiently removed, while if over 350° C., the catalyst deteriorates.

The catalyst may be supported on a carrier by any methods. For example, the above-mentioned liquid mixture in a slurry or solution state is impregnated into a carrier to be supported on the carrier, or is kneaded with a carrier powder, or the heteropoly-acid salt is deposited on the carrier, for example, by coating.

The space time yield, selectivity, and degree of conversion as described in this specification are defined as follows:

Space time yield = Amount of ester synthesized per unit time (g/h)/Amount of catalyst ($\lambda$ or kg)

Yield = Number of moles of ester synthesized/Number of moles of acid supplied $\times 100$ Degree of conversion = Number of moles of reacted acid/Number of moles of supplied acid $\times 100$ Below, the present invention will be further explained using examples, which do not however limit the present invention in any way.

EXAMPLE 1

Fifteen grams (about 0.0438 mole) of commercially available phosphotungstic acid (made by Wako Junyaku) and 60 cc of pure water were placed in a 300 cc flask and the former dissolved in the latter.

Separately, 21.5 g (0.110 mole) of cesium nitrate ($CsNO_3$) was dissolved in water. This was dropped in the above-mentioned aqueous phosphotungstic acid solution, while stirring, using a dropping funnel. At this time, fine white crystals of cesium phosphotungstate were precipitated simultaneously with the dropping. The water in the flask where the white particulates precipitated was evaporated off using a hot water bath. The solid mass obtained by removal of the water was taken out onto a laboratory dish and placed into a dryer, where it was dried in the air at 150° C. for 6 hours. The dried product was pulverized and was sieved to separate out particles of 1 to 2 mm size. Thirty-five cc of this was packed into a reaction tube and used for the reaction.

The reaction was performed while maintaining a temperature of 180° C. and a reaction pressure of 5 $kg/cm^2G$ and by passing a mixed gas of acrylic acid, ethylene, and water vapor of a volume ratio of 1:18:1 under standard conditions at a flow rate of 35 $\lambda$/hr. The effluent and the gas four hours after starting to pass the mixed gas were sampled and measured by gas chromatography, whereupon the degree of conversion of acrylic acid was found to be 87.1 percent and the yield of ethyl acrylate with respect to acrylic acid was 79.3 percent. The space time yield of ethyl acrylate obtained was 177 g/hr·$\lambda$ catalyst.

EXAMPLE 2

The same procedure was performed as in Example 1, except that use was made of 29.3 grams (0.110 mole) of thallium nitrate ($T\lambda NO_3$) instead of cesium nitrate.

EXAMPLE 3

The same procedure was performed as in Example 1, except that use was made of 12.7 grams (0.055 mole) of rubidium carbonate ($Rb_2CO_3$) instead of cesium nitrate.

EXAMPLE 4

The same procedure was performed as in Example 1, except that use was made of 11.1 grams (0.110 mole) of potassium nitrate ($KNO_3$) instead of cesium nitrate.

EXAMPLE 5

The same procedure was performed as in Example 1, except that use was made of 8.8 grams (0.110 mole) of ammonium nitrate ($NH_4NO_3$) instead of cesium nitrate.

COMPARATIVE EXAMPLE 1

The same procedure was performed as in Example 1, except that commercially available phosphotungstic acid (made by Wako Junyaku) was dried at 150° C. for 6 hours, then was formed into a tablet, which was in turn pulverized and sieved to obtain the particles of 1 to 2 mm size, 35 cc of which was used as the catalyst.

EXAMPLE 6

The same procedure was performed as in Example 1, except that use was made of propylene instead of ethylene, to form isopropyl acrylate.

EXAMPLE 7

Using as a catalyst 10.7 cc of cesium salt of the phosphotungstic acid used as a catalyst in Example 1 and at a reaction temperature of 150° C. and a reaction pressure held at ordinary pressure, a mixed gas of acetic acid, ethylene, and water vapor in a volumetric ratio of 6.8:92.2:1 was passed under standard conditions at a flow rate of 10.7 $\lambda$/hr. Four hours after the mixed gas was started being passed, the effluent and gas were sampled and analyzed by gas chromatography, whereupon it was found that the degree of conversion of acetic acid was 52.6 percent and the yield of ethyl acetate with respect to acetic acid was 50.0 percent. The space time yield of ethyl acetate found from this result was 134 g/hr·$\lambda$ catalyst.

EXAMPLE 8

The same procedure was performed as in Example 7 except that use was made of thallium phosphotungstate as the catalyst.

EXAMPLE 9

The same procedure was performed as in Example 7 except that use was made of rubidium phosphotungstate as the catalyst.

EXAMPLE 10

The same procedure was performed as in Example 7 except that use was made of potassium phosphotungstate as the catalyst.

EXAMPLE 11

The same procedure was performed as in Example 7 except that use was made of ammonium phosphotungstate as the catalyst.

EXAMPLE 12

The same procedure was performed as in Example 7 except that use was made of potassium phosphotungstate as the catalyst and use was made of propylene instead of ethylene.

EXAMPLE 13

The same procedure was performed as in Example 7 except that the reaction pressure was made 5 kg/cm$^2$G.

COMPARATIVE EXAMPLE 2

The same procedure was performed as in Example 7 except that the same catalyst as in Comparative Example 1 was used.

The results of the above-mentioned Examples 1 to 13 and Comparative Examples 1 and 2 are shown all together in Table 1. Note that the results of Example 1 etc. are already shown, but are given again for comparative purposes. In the above-mentioned Examples 1 to 13, the operation was continued for 96 hours, but the yield and space time yield of the target components of acrylic acid or acetic acid did not fall much at all, while in Comparative Examples 1 and 2 the yield fell 2 to 5 percent in 20 hours.

TABLE 1

| | Catalyst | | | Material mixed gas | | Reaction conditions | | |
|---|---|---|---|---|---|---|---|---|
| Ex. | Name | Catalyst size (mm) | Am't of catalyst used (cc) | Name Volume ratio | | Reaction temp. (°C.) | Reaction pressure (kg/cm$^2$ G) | Flow rate under standard conditions (Nl/hr) |
| Ex. 1 | Cesium phosphotungstate | 1 to 2 | 35 | Acrylic acid:Ethylene:Water vapor | 1:18:1 | 180 | 5 | 35 |
| Ex. 2 | Thallium phosphotungstate | " | " | Acrylic acid:Ethylene:Water vapor | 1:18:1 | " | " | " |
| Ex. 3 | Rubidium phosphotungstate | " | " | Acrylic acid:Ethylene:Water vapor | 1:18:1 | " | " | " |
| Ex. 4 | Potassium phosphotungstate | " | " | Acrylic acid:Ethylene:Water vapor | 1:18:1 | " | " | " |
| Ex. 5 | Ammonium phosphotungstate | " | " | Acrylic acid:Ethylene:Water vapor | 1:18:1 | " | " | " |
| Ex. 6 | Cesium phosphotungstate | " | " | Acrylic acid:Propylene:Water vapor | 1:18:1 | " | " | " |
| Ex. 7 | Cesium phosphotungstate | " | 10.7 | Acetic acid:Ethylene:Water vapor | 6.8:92.2:1 | 150 | 0 | 10.7 |
| Ex. 8 | Thallium phosphotungstate | " | " | Acetic acid:Ethylene:Water vapor | 6.8:92.2:1 | " | " | " |
| Ex. 9 | Rubidium phosphotungstate | " | " | Acetic acid:Ethylene:Water vapor | 6.8:92.2:1 | " | " | " |
| Ex. 10 | Potassium phosphotungstate | " | " | Acetic acid:Ethylene:Water vapor | 6.8:92.2:1 | " | " | " |
| Ex. 11 | Ammonium phosphotungstate | " | " | Acetic acid:Ethylene:Water vapor | 6.8:92.2:1 | " | " | " |
| Ex. 12 | Potassium phosphotungstate | " | " | Acetic acid:Propylene:Water vapor | 6.8:92.2:1 | " | " | " |
| Ex. 13 | Cesium phosphotungstate | " | " | Acetic acid:Ethylene:Water vapor | 6.8:92.2:1 | " | 5 | " |
| Comp. Ex. 1 | Phosphotungstic acid | " | 35 | Acrylic acid:Ethylene:Water vapor | 1:18:1 | 180 | 5 | 35 |
| Comp. Ex. 2 | Phosphotungstic acid | " | 10.7 | Acetic acid:Ethylene:Water vapor | 6.8:92.2:1 | 150 | 0 | 10.7 |

| | | Results | | |
|---|---|---|---|---|
| Ex. | Target product | Degree of conversion of acrylic or acetic acid (%) | Yield of target product by acrylic/acetic acid (%) | Space time yield (g/hr · l catalyst) |
| Ex. 1 | Ethyl acrylate | 87.1 | 79.3 | 177 |
| Ex. 2 | Ethyl acrylate | 86.1 | 77.5 | 173 |
| Ex. 3 | Ethyl acrylate | 87.8 | 79.9 | 178 |
| Ex. 4 | Ethyl acrylate | 58.7 | 54.0 | 121 |
| Ex. 5 | Ethyl acrylate | 83.3 | 75.4 | 168 |
| Ex. 6 | Isopropyl acrylate | 62.5 | 56.3 | 145 |
| Ex. 7 | Ethyl acetate | 52.6 | 50.0 | 134 |

TABLE 1-continued

|  |  |  |  |  |
|---|---|---|---|---|
| Ex. 8 | Ethyl acetate | 64 | 62.4 | 167 |
| Ex. 9 | Ethyl acetate | 57.4 | 55.1 | 148 |
| Ex. 10 | Ethyl acetate | 65.0 | 64.0 | 172 |
| Ex. 11 | Ethyl acetate | 60.4 | 59.5 | 159 |
| Ex. 12 | Isopropyl acetate | 56.6 | 53.8 | 167 |
| Ex. 13 | Ethyl acetate | 92.3 | 90.5 | 243 |
| Comp. Ex. 1 | Ethyl acrylate | 41.0 | 31.5 | 70 |
| Comp. Ex. 2 | Ethyl acetate | 6.5 | 6.3 | 17 |

EXAMPLE 14

One hundred and fifty grams (about 0.0438 mole) of commercially available phosphotungstic acid (made by Wako Junyaku) and 60 cc of pure water were placed in a 300 cc flask and the former was dissolved in the latter.

Separately, 21.5 g (0.110 mole) of cesium nitrate ($CsNO_3$) was dissolved in water. This was dropped in the above-mentioned aqueous phosphotungstic acid solution, while stirring, using a dropping funnel. At this time, white particulate crystals of cesium phosphotungstate were precipitated simultaneously with the dropping. To this was added and stirred in 500 cc of silica of 1 to 2 mm diameter. The water in the flask was evaporated off using a hot water bath. After the water was driven off, the sample as placed in a dryer and dried in the air at 150° C. for 6 hours. Thirty-five cc of the dried silica supporting the catalyst was packed into a reaction tube and used for the reaction.

The reaction was performed while maintaining a temperature of 180° C. and a reaction pressure of 5 kg/cm²G and by passing a gas of acrylic acid, ethylene, and water vapor of a volume ratio of 1:18:1 in a standard state at a flow rate of 35 λ/hr. The effluent and the gas four hours after starting to pass the mixed gas were sampled and measured by gas chromatography, whereupon the degree of conversion of acrylic acid was found to be 48.6 percent and the yield of ethyl acrylate with respect to acrylic acid was 45.0 percent. The space time yield of ethyl acrylate obtained was 100 g/hr·λ catalyst.

EXAMPLE 15

Using a 300 cc flask, 60 cc of pure water was added to 150 g (0.0453 mole) of commercially available silicotungstic acid (made by Wako Junyaku) to dissolve the same. Separately, 22.1 g (0.1133 mole) of cesium nitrate ($CsNO_3$) was dissolved to make an aqueous solution, which was dropped into the aqueous solution of silicotungstic acid, while stirring, using a drop funnel. White particulate crystals were precipitated simultaneously with the dropping. The 300 cc flask was placed in a hot water bath and the majority of the water in the flask was evaporated off in a boiling state. The solid mass obtained was taken out onto a laboratory dish and placed into a dryer, where it was dried in the air at 150° C. for 6 hours. The dried product was pulverized and was sieved to separate out particles of 1 to 2 mm size. Thirty-five cc of this was packed into a reaction tube and used for the reaction.

The reaction was performed while maintaining a temperature of 180° C. and a reaction pressure of 5 kg/cm²G and by passing a mixed gas of acrylic acid, ethylene, and water vapor of a volume ratio of 1:18:1 under standard conditions at a flow rate of 35 λ/hr. The degree of conversion of the acrylic acid 4 hours after the gas started to be passed was found to be 86.6 percent and the yield (gas chromatography analysis) was 78.1 percent. The space time yield of ethyl acrylate obtained was 174 g/hr·λ catalyst.

EXAMPLE 16

The catalyst was prepared by the same method as in Example 15, except that use was made of 30.2 grams (0.1134 mole) of thallium nitrate ($TlNO_3$) instead of cesium nitrate, and the reaction was performed under the same reaction conditions as in Example 15. The results are shown in Table 2.

EXAMPLE 17

The catalyst was prepared by the same method as in Example 15, except that use was made of 13.1 grams (0.0566 mole) of rubidium carbonate ($Rb_2CO_3$) instead of cesium nitrate, and the reaction was performed under the same reaction conditions as in Example 15. The results are shown in Table 2.

EXAMPLE 18

The catalyst was prepared by the same method as in Example 15, except that use was made of 9.1 grams (0.1133 mole) of ammonium nitrate ($NH_4NO_3$) instead of cesium nitrate, and the reaction was performed under the same reaction conditions as in Example 15. The results are shown in Table 2.

EXAMPLE 19

The catalyst was prepared by the same method as in Example 15, except that use was made of 11.4 grams (0.1133 mole) of potassium nitrate ($KNO_3$) instead of cesium nitrate, and the reaction was performed under the same reaction conditions as in Example 15. The results are shown in Table 2.

COMPARATIVE EXAMPLE 3

The reaction was performed under the same reaction conditions as in Example 15, except that commercially available silicotungstic acid was dried at 150° C. for 6 hours, then molded into tablet form, which was pulverized and sieved to separate the particles of 1 to 2 mm size, of which 35 cc was used as the catalyst for the reaction. The results are shown in Table 2.

EXAMPLE 20

The reaction was performed under the same reaction conditions as in Example 15, except that the same catalyst as Example 15 (Cs salt of silicotungstic acid) was used and use was made of propylene instead of ethylene. The results of the reaction of the isopropyl acrylate produced are shown in Table 2.

EXAMPLE 21

Using 9.7 cc of the same catalyst as in Example 15 (Cs salt of silicotungstic acid), a temperature of 150° C., and a reaction pressure held at ordinary pressure, a mixed gas of acetic acid and ethylene (volumetric ratio of 6.8:93.2) was passed at a flow rate of 9.7 λ/hr (converted as being under standard conditions). The degree of conversion of acetic acid 4 hours after the gas started to be passed was 47.5 percent and the yield was 46.3 percent (gas chromatography analysis). The space time yield of ethyl acetate found from the results was 124 g/λ·hr.

EXAMPLE 22

Using the same catalyst as in Example 15, the reaction was performed under the same reaction 10, conditions as in Example 21 except that the reaction pressure was made 5 kg/cm$^2$G. The degree of conversion of acetic acid 4 hours after the gas began to be passed was 88.5 percent and the yield was 86.9 percent. The space time yield of ethyl acetate found from the results was 233 g/λ·hr.

EXAMPLE 23

The reaction was performed under the same reaction conditions as in Example 21 except that use was made of the same catalyst as in Example 16 (Tl salt of silicotungstic acid). The results are shown in Table 3.

EXAMPLE 24

The reaction was performed under the same reaction conditions as in Example 21, except that use was made of the same catalyst as in Example 17 (Rb salt of silicotungstic acid). The results are shown in Table 3.

EXAMPLE 25

The reaction was performed under the same reaction conditions as in Example 21, except that use was made of the same catalyst as in Example 18 (NH$_4$ salt of silicotungstic acid). The results are shown in Table 3.

EXAMPLE 26

The reaction was performed under the same reaction conditions as in Example 21, except that use was made of the same catalyst as in Example 19 (K salt of silicotungstic acid). The results are shown in Table 3.

COMPARATIVE EXAMPLE 4

The reaction was performed under the same reaction conditions as in Example 21, except that use was made of the same catalyst as in Comparative Example 3 (silicotungstic acid). The results are shown in Table 3.

EXAMPLE 27

The reaction was performed under the same reaction conditions as in Example 21, except that use was made of the same catalyst as in Example 15 (Cs salt of silicotungstic acid) and use was made of propylene instead of ethylene. The reaction results of isopropyl acetate formed are shown in Table 3.

TABLE 2

| Ex. No. | Catalyst | Acrylic Acid Ester | | Space time yield (g/l · hr) |
|---|---|---|---|---|
| | | Acrylic acid degree of conversion (%) | Acrylic acid ester yield (%) | |
| 15 | Cs salt of silicotungstic acid | 86.6 | 78.1 | 174 |
| 16 | Tl salt of silicotungstic acid | 77.3 | 72.8 | 162 |
| 17 | Rb salt of silicotungstic acid | 79.3 | 72.8 | 162 |
| 18 | NH$_4$ salt of silicotungstic acid | 27.2 | 23.4 | 52 |
| 19 | K salt of silicotungstic acid | 12.9 | 11.0 | 25 |
| 20 | Cs salt of silicotungstic acid | 66.5 | 56.5 | 151 |
| Comp. Ex. 3 | Silicotungstic acid | 9.1 | 7.3 | 17 |

EXAMPLES 15 TO 19 AND COMPARATIVE EXAMPLE 3

Amount of catalyst: 35 cc, Reaction temperature: 180° C., reaction pressure: 5 kg/cm$^2$G, Volumetric ratio of materials: Acrylic acid:Ethylene:Water=1:18:1, Amount of material feed:35 λ/hr (under standard conditions)

EXAMPLE 20

Volumetric ratio of materials:Acrylic acid:-Propylene:Water=1:18:1, rest the same.

TABLE 3

| Ex. No. | Catalyst | Acetic Acid Ester | | Space time yield (g/l · hr) |
|---|---|---|---|---|
| | | Acetic acid degree of conversion (%) | Acetic acid ester yield (%) | |
| 21 | Cs salt of silicotungstic acid | 47.5 | 46.3 | 124 |
| 22 | Cs salt of silicotungstic acid | 88.5 | 86.9 | 233 |
| 23 | Tl salt of silicotungstic acid | 35.1 | 34.9 | 93 |
| 24 | Rb salt of silicotungstic acid | 37.5 | 36.4 | 97 |
| 25 | NH$_4$ salt of silicotungstic acid | 28.7 | 27.6 | 74 |
| 26 | K salt of silicotungstic acid | 9.7 | 9.7 | 26 |
| 27 | Cs salt of silicotungstic acid | 36.5 | 33.5 | 104 |
| Comp. Ex. 4 | Silicotungstic acid | 1.3 | 1.0 | 3 |

(1) EXAMPLES 21 AND 23 TO 26 AND COMPARATIVE EXAMPLE 4

Amount of catalyst: 9.7 cc, Reaction temperature: 150° C., Reaction pressure: ordinary pressure, Volumetric ratio of materials: Acetic acid:Ethylene=6.8:93.2, Amount of material feed: 9.7 λ/hr (under standard conditions)

(2) EXAMPLE 22

Reaction pressure: 5 kg/cm²G, otherwise same as conditions of (1).

(3) EXAMPLE 27

Volumetric ratio of materials: Acetic acid:propylene=6.8:93.2, otherwise same as conditions of (1).

EXAMPLE 28

Using a 1 liter flask, 60 cc of pure water was added to 125 g of commercially available phosphomolybdic acid (made by Wako Junyaku) to dissolve the same. Separately, 25.7 g of cesium nitrate (CsNO₃) was dissolved to make an aqueous solution which was dropped into the above-mentioned aqueous phosphomolybdic acid solution while stirring using a drop funnel. Simultaneous with the dropping, particulate crystals were precipitated. The 1 liter flask was placed in a hot water bath and the majority of the water in the flask was evaporated off. The resultant solid mass was taken out on a laboratory dish which was placed in a dryer to dry the solid mass in the air at 150° C. for 13 hours. The dried product was pulverized and then sieved to separate the particles of 1 to 2 mm size, 10.7 cc of which was used as the catalyst and supplied to the reaction.

While maintaining the reaction temperature at 150° C. and the reaction pressure at ordinary pressure, a mixed gas of acetic acid, ethylene, and water vapor (volumetric ratio of 6.8:92.2:1) was passed at a flow rate of 10.7 λ/hr (converted as being under standard condition). Four hours after the gas began to be passed, the degree of conversion of acetic acid was 18.8 percent and the yield was 18.6 percent (gas chromatography). The space time yield of ethyl acetate found from the results was 50 g/hr·λ.

EXAMPLE 29

The same procedure was performed as in Example 28, except that use was made of 35.2 g of thallium nitrate (TlNO₃) instead of cesium nitrate.

EXAMPLE 30

The same procedure was performed as in Example 28, except that use was made of 15.3 g of rubidium carbonate (Rb₂CO₃) instead of cesium nitrate.

EXAMPLE 31

The same procedure was performed as in Example 28, except that use was made of 10.6 g of ammonium nitrate (NH₄NO₃) instead of cesium nitrate.

EXAMPLE 32

The same procedure was performed as in Example 28, except that use was made of 13.3 g of potassium nitrate (KNO₃) instead of cesium nitrate.

COMPARATIVE EXAMPLE 5

A 125 g amount of commercially available phosphomolybdic acid was dried at 150° C. for 13 hours, then was formed into tablets. This was pulverized and sieved to separate the particles of 1 to 2 mm size. Of this, 10.7 cc was used as a catalyst and supplied to the reaction. Otherwise, the same procedure was performed as in Example 28.

EXAMPLE 33

The same procedure was performed as in Example 28, except that the same catalyst as in Example 28 (Cs salt of phosphomolybdic acid) was used and acrylic acid was used instead of acetic acid.

EXAMPLE 34

The same procedure was performed as in Example 28, except that the same catalyst as in Example 28 (Cs salt of phosphomolybdic acid) was used and propylene was used instead of ethylene.

EXAMPLE 35

Using a 1 liter flask, 60 cc of pure water was added to 125 g of commercially available silicomolybdic acid to dissolve the same. Separately, 26.1 g of cesium nitrate (CsNO₃) was dissolved to form an aqueous solution. The same procedure after this as in Example 28 was performed to prepare the catalyst and perform the reaction.

COMPARATIVE EXAMPLE 6

A 125 g amount of commercially available silicomolybdic acid was dried at 150° C. for 13 hours, then formed into tablets. This was pulverized and sieved to separate the particles of 1 to 2 mm size. Of this, 10.7 cc was used as the catalyst and supplied to the reaction. Otherwise, the same procedure as in Example 28 was performed.

The results of the above Examples 28 to 35 and Comparative Examples 5 and 6 are shown together in Table 4.

In the above Examples 28 to 35, the operation as continued for 100 hours, but the space time yield of the target component with respect to acetic acid or acrylic acid did not fall much at all, while the yield fell 2 to 5 percent in 20 hours in the case of the Comparative Examples 5 and 6.

TABLE 4

| | Name | Name Volume ratio | Reaction temp. (°C.) | Reaction pressure (kg/cm²G) | Flow rate under standard conditions (#/hr) | Target product | Degree of conversion of acetic or acrylic acid (%) | Yield of target product by acetic/acrylic acid (%) | Space time yield (g/hr·l catalyst) |
|---|---|---|---|---|---|---|---|---|---|
| Ex. 28 | Cesium phosphomolybdate | Acetic acid:Ethylene: Water vapor 6.8:92.2:1 | 150 | 1 | 10.7 | Ethyl acetate | 18.8 | 18.6 | 50 |
| Ex. 29 | Thallium phosphomolybdate | Acetic acid:Ethylene: Water vapor 6.8:92.2:1 | 150 | 1 | 10.7 | Ethyl acetate | 23.0 | 22.3 | 60 |
| Ex. 30 | Rubidium phosphomolybdate | Acetic acid:Ethylene: Water vapor 6.8:92.2:1 | 150 | 1 | 10.7 | Ethyl acetate | 21.1 | 20.5 | 55 |
| Ex. 31 | Ammonium phosphomolybdate | Acetic acid:Ethylene: Water vapor 6.8:92.2:1 | 150 | 1 | 10.7 | Ethyl acetate | 22.0 | 21.6 | 58 |

TABLE 4-continued

|  | Name | Name Volume ratio | Reaction temp. (°C.) | Reaction pressure (kg/ cm² G) | Flow rate under standard conditions (#/hr) | Target product | Degree of conversion of acetic or acrylic acid (%) | Yield of target product by acetic/acrylic acid (%) | Space time yield (g/hr· l catalyst) |
| --- | --- | --- | --- | --- | --- | --- | --- | --- | --- |
| Ex. 32 | Potassium phosphomolybdate | Acetic acid:Ethylene: Water vapor 6.8:92.2:1 | 150 | 1 | 10.7 | Ethyl acetate | 24.2 | 23.8 | 64 |
| Ex. 33 | Cesium phosphomolybdate | Acetic acid:Ethylene: Water vapor 6.8:92.2:1 | 150 | 1 | 10.7 | Ethyl acrylate | 19.2 | 18.6 | 57 |
| Ex. 34 | Cesium phosphomolybdate | Acetic acid:Propylene: Water vapor 6.8:92.2:1 | 150 | 1 | 10.7 | Isopropyl acetate | 21.0 | 19.3 | 60 |
| Ex. 35 | Silicomolybdic acid | Acetic acid:Ethylene: Water vapor 6.8:92.2:1 | 150 | 1 | 10.7 | Ethyl acetate | 21.0 | 20.5 | 55 |
| Comp. Ex. 5 | Phosphomolybdic acid | Acetic acid:Ethylene: Water vapor 6.8:92.2:1 | 150 | 1 | 10.7 | Ethyl acetate | 4.8 | 4.5 | 12 |
| Comp. Ex. 6 | Silicomolybdic acid | Acetic acid:Ethylene: Water vapor 6.8:92.2:1 | 150 | 1 | 10.7 | Ethyl acetate | 5.9 | 5.6 | 15 |

EXAMPLE 36

Using a 1 liter flask, 250 g of phosphomolybdotungstic acid (made by Nihon Mukikagaku) was dissolved in 175 cc of pure water. To this was dropped 50 g of cesium nitrate (made by Wako Junyaku) dissolved in 400 cc pure water. A yellow precipitate was obtained.

The water content in the precipitated deposit was evaporated off in a hot water bath until a slurry state was reached, then this was dried in air at 150° C. for 3 hours. The dried product was pulverized, the particles of 1 to 2 mm size were taken, and this was sintered in the air at 200° C. for 5 hours.

Ten g of the sintered product obtained by this procedure was supplied to the reaction as a catalyst.

Mixed gas of a volumetric ratio of acetic acid:ethylene:water vapor of 6.8:92.2:1 was introduced at a flow rate of 10.7 λ/hr and a reaction performed with a reaction temperature of 150° C. and a pressure of 5 kg/cm²G.

The gas from the reaction was cooled and condensed to collect the liquid reaction product. This was analyzed by gas chromatography and evaluated as to activity. As a result, the degree of conversion of the acetic acid was 65.1 percent and the yield was 64.7 percent. The space time yield of acetic acid found from this was 185 g/hr·kg.

EXAMPLE 37

Using a 1 liter flask, 25 g of phosphomolybdotungstic acid (made by Nihon Mukikagaku) was dissolved in 25 cc of pure water. To this was added 100 cc of a silica carrier for impregnation and supporting of the same. The catalyst-supported carrier was dried and sintered under the same conditions as with Example 36. The result was supplied to the reaction as a catalyst under the same conditions as in Example 38. The rate of the catalyst supported was 25 percent by weight.

As a result, the degree of conversion of acetic acid was 90.0 percent and the yield was 88.5 percent. The space time yield found from this was 253 g/hr·kg.

COMPARATIVE EXAMPLE 7

The same procedure was performed as in Example 36, except that use was made of phosphotungstic acid (made by Nihon Mukikagaku) instead of phosphomolybdotungstic acid and the amount of cesium nitrate was made 36 g.

COMPARATIVE EXAMPLE 8

The same procedure was performed as in Example 36, except that use was made of phosphomolybdic acid (made by Wako Junyaku) instead of phosphomolybdotungstic acid and the amount of cesium nitrate was made 52 g.

COMPARATIVE EXAMPLE 9

The same procedure was performed as in Example 37, except that use was made of phosphotungstic acid (made by Nihon Mukikagaku) instead of phosphomolybdotungstic acid.

COMPARATIVE EXAMPLE 10

The same procedure was performed as in Example 37, except that use was made of phosphomolybdic acid (made by Wako Junyaku) instead of phosphomolybdotungstic acid.

The results of the above are shown in Table 5.

TABLE 5

|  | Name | Am't of catalyst used (g) | Material mixed gas Name Volume ratio | Reaction temp. (°C.) | Reaction pressure (kg/ cm² G) | Flow rate under standard conditions (Nl/hr) | Degree of conversion of acetic acid (%) | Yield of ethyl acetate (%) | Space time yield (g/hr. kg catalyst) |
| --- | --- | --- | --- | --- | --- | --- | --- | --- | --- |
| Ex. 36 | Cesium phosphotungstomolybdate | 10 | Acetic acid:Ethylene: Water vapor 6.8:92.2:1 | 150 | 5 | 10.7 | 65.1 | 64.7 | 185 |
| Ex. 38 | Impregnated and supported phosphotungstomolybdic acid | " | Acetic acid:Ethylene: Water vapor 6.8:92.2:1 | " | " | " | 90.0 | 88.5 | 253 |
| Comp. Ex. 7 | Cesium phosphotungstate | " | Acetic acid:Ethylene: Water vapor 6.8:92.2:1 | " | " | " | 62.4 | 60.8 | 174 |
| Comp. Ex. 8 | Cesium phosphomolybdate | " | Acetic acid:Ethylene: Water vapor 6.8:92.2:1 | " | " | " | 37.5 | 37.4 | 107 |
| Comp. | Impregnated and | " | Acetic acid:Ethylene: | " | " | " | 63.3 | 62.2 | 178 |

TABLE 5-continued

| | Name | Am't of catalyst used (g) | Material mixed gas Name Volume ratio | Reaction temp. (°C.) | Reaction pressure (kg/cm² G) | Flow rate under standard conditions (Nl/hr) | Degree of conversion of acetic acid (%) | Yield of ethyl acetate (%) | Space time yield (g/hr. kg catalyst) |
|---|---|---|---|---|---|---|---|---|---|
| Ex. 9 | supported type phosphotungstic acid | | Water vapor 6.8:92.2:1 | | | | | | |
| Comp. Ex. 10 | Impregnated and supported phosphomolybdic acid | " | Acetic acid:Ethylene: Water vapor 6.8:92.2:1 | " | " | " | 17.8 | 17.8 | 51 |

EXAMPLE 38

A 125 g amount of commercially available of pure water were placed into a 1 liter flask and dissolved.

Separately, 12.0 g of barium nitrate (Ba(NO$_3$)$_2$) was dissolved in water and this was dropped into the above aqueous phosphotungstic acid solution, while stirring, using a dropping funnel. The water in the flask was evaporated out using a hot water bath. The solid mass from which the water was removed was taken out on a laboratory dish, placed in a dryer, and dried in the air at 150° C. for 13 hours, then was formed into tablets. This was pulverized and sieved to separate out the particles of 1 to 2 mm size. Of this, 10.7 cc was packed into a reaction tube and supplied to the reaction as a catalyst.

The reaction was performed while maintaining a temperature of 150° C. and an ordinary reaction pressure and passing a mixed gas of a volumetric ratio of acetic acid, ethylene, and water vapor of 6.8:92.2:1 in a standard state at a flow rate of 10.7 λ/hr. Four hours after the mixed gas was started to be passed, the effluent and gas were sampled and analyzed by gas chromatography, whereupon the degree of conversion of acetic acid was 18.2 percent and the yield of ethyl acetate with respect to acetic acid was 17.9 percent. The space time yield of the ethyl acetate found from the results was 48 g/hr·λ catalyst.

EXAMPLE 39

The same procedure was performed as in Example 38, except that 21.3 g of solid gold chloride (AuCλ) was added as is instead of barium nitrate.

EXAMPLE 40

The same procedure was performed as in Example 38, except that 3.11 g of sodium nitrate (NaNO$_3$) was used instead of barium nitrate.

EXAMPLE 41

The same procedure was performed as in Example 38, except that use was made of acrylic acid instead of acetic acid.

EXAMPLE 42

The same procedure was performed as in Example 38, except that use was made of propylene instead of ethylene.

COMPARATIVE EXAMPLE 11

The same procedure was performed as in Example 38, except that use was made of the catalyst of Comparative Example 1 and use was made of acrylic acid instead of acetic acid.

COMPARATIVE EXAMPLE 12

The same procedure was performed as in Example 38, except that use was made of 11.7 g of magnesium nitrate (Mg(NO$_3$)$_2$.6H$_2$O) instead of barium nitrate.

COMPARATIVE EXAMPLE 13

The same procedure was performed as in Example 38, except that use was made of 8.9 g of indium chloride (InCl$_3$.4H$_2$O) instead of barium nitrate.

COMPARATIVE EXAMPLE 14

The same procedure was performed as in Example 38, except that use was made of 11.6 g of yttrium nitrate (Y(NO$_3$)$_3$.6H$_2$O) instead of barium nitrate.

The results of the above Examples 38 to 42 and Comparative Examples 11 to 14 are shown together with the results of Comparative Example 1 in Table 6. In Examples 38 to 42, the operation was continued for 100 hours, but there was almost no decline in the yield of the target component with respect to acetic acid or acrylic acid or in the space time yield. In Comparative Example 11, however, the yield fell 2 to 5 percent in 20 hours.

TABLE 6

| | | | Reaction conditions | | | | |
|---|---|---|---|---|---|---|---|
| | Name | Material mixed gas Name Volume ratio | Reaction temp. (°C.) | Reaction pressure (kg/cm² G) | Flow rate under standard conditions (Nl/hr) | Target product | Degree of conversion of acetic or acrylic acid (%) |
| Ex. 38 | Barium phosphotungstate | Acetic acid:Ethylene:Water vapor 6.8:92.2:1 | 150 | 0 | 10.7 | Ethyl acetate | 18.2 |
| Ex. 39 | Gold phosphotungstate | Acetic acid:Ethylene:Water vapor 6.8:92.2:1 | 150 | 0 | 10.7 | Ethyl acetate | 18.5 |
| Ex. 40 | Sodium phosphotungstate | Acetic acid:Ethylene:Water vapor 6.8:92.2:1 | 150 | 0 | 10.7 | Ethyl acetate | 15.5 |
| Ex. 41 | Barium phosphotungstate | Acetic acid:Ethylene:Water vapor 6.8:92.2:1 | 150 | 0 | 10.7 | Ethyl acrylate | 19.0 |
| Ex. 42 | Barium phosphotungstate | Acetic acid:Propylene:Water vapor 6.8:92.2:1 | 150 | 0 | 10.7 | Isopropyl acetate | 14.0 |
| Comp. | Phosphotungstic acid | Acetic acid:Ethylene:Water vapor | 150 | 0 | 10.7 | Ethyl | 6.5 |

TABLE 6-continued

| | | | | | | | |
|---|---|---|---|---|---|---|---|
| Ex. 1 | | 6.8:92.2:1 | | | | acetate | |
| Comp. Ex. 11 | Phosphotungstic acid | Acetic acid:Ethylene:Water vapor 6.8:92.2:1 | 150 | 0 | 10.7 | Ethyl acrylate | 7.0 |
| Comp. Ex. 12 | Magnesium phosphotungstate | Acetic acid:Ethylene:Water vapor 6.8:92.2:1 | 150 | 0 | 10.7 | Ethyl acetate | 0.38 |
| Comp. Ex. 13 | Indium phosphotungstate | Acetic acid:Ethylene:Water vapor 6.8:92.2:1 | 150 | 0 | 10.7 | Ethyl acetate | 0.38 |
| Comp. Ex. 14 | Yttrium phosphotungstate | Acetic acid:Ethylene:Water vapor 6.8:92.2:1 | 150 | 0 | 10.7 | Ethyl acetate | 0.077 |

| | Yield of target product by acetic/acrylic acid (%) | Space yield (g/hr · l catalyst) | Ion radius of metal (Å) |
|---|---|---|---|
| Ex. 38 | 17.9 | 48 | 1.49 |
| Ex. 39 | 17.9 | 48 | 1.51 |
| No. 40 | 14.9 | 40 | 1.16 |
| No. 41 | 17.8 | 54 | 1.49 |
| No. 42 | 13.2 | 41 | 1.49 |
| Comp. Ex. 1 | 6.3 | 17 | — |
| Comp. Ex. 11 | 6.6 | 20 | — |
| Comp. Ex. 12 | 0.37 | 1 | 0.86 |
| Comp. Ex. 13 | 0.37 | 1 | 0.94 |
| Comp. Ex. 14 | 0.075 | 0.2 | 1.04 |

EXAMPLE 43

A 69.9 percent by weight of an aqueous solution of commercially available phosphotungstic acid was placed in a 1 liter flask. To this was dropped in small amounts at a time, while stirring, 0.1 mole of an aqueous solution of lithium nitrate per mole of phosphotungstic acid.

In the aqueous solution obtained here, 250 cc of silica carrier (5 mmφ) was immersed and made to absorb the full amount of the liquid, then this was dried at 150° C. for 3 hours and further at 200° C. for 5 hours to prepare a supported catalyst with a 50 percent by weight of supporting rate.

Ten g of the prepared catalyst was packed into a reaction tube and the reaction was performed at a temperature of 150° C. and a pressure of 5 kg/cm²G while introducing a mixed gas off acetic acid, ethylene, and water vapor of a volumetric ratio of 6.8:92.2:1 at a flow rate of 10.7 Nλ/hr.

The formed gas was cooled and condensed to collect the liquid reaction product which was then analyzed by gas chromatography.

As a result, the yield of ethyl acetate was 91.8 percent.

EXAMPLE 44

The catalyst was prepared by the same process as in Example 43, except for the use of copper nitrate instead of lithium nitrate, to obtain a catalyst with a 50 percent by weight supporting rate.

The catalyst obtained was used for performing a reaction under the same reaction conditions as in Example 43. As a result, the yield of ethyl acetate was 86.3 percent.

COMPARATIVE EXAMPLE 15

Into a 69.9 percent by weight aqueous solution of commercially available phosphotungstic acid, 250 cc of silica carrier (5 mmφ) was immersed and made to absorb the entire amount of the liquid, then the result was dried at 150° C. for 3 hours and at 200° C. for 5 hours to prepare a catalyst having a supporting rate of 50 percent by weight.

The obtained catalyst was used to perform a reaction under the same reaction conditions as in Example 43. As a result, the yield of ethyl acetate was 84.6 percent.

The results are shown in Table 7.

TABLE 7

| | Name | Am't of catalyst used (cc) | Material mixed gas Name Volume ratio | Reaction temp. (°C.) | Reaction pressure (kg/cm² G) | Flow rate under standard conditions (#/hr) | Degree of conversion of acetic acid (%) | Yield of ethyl acetate (%) |
|---|---|---|---|---|---|---|---|---|
| | | | | Reaction conditions | | | | |
| Ex. 45 | Lithium phosphotungstate | 10 | Acetic acid:Ethylene: Water vapor 6.8:92.2:1 | 150 | 5 | 10.7 | 92.9 | 91.8 |
| Ex. 46 | Copper phosphotungstate | 10 | Acetic acid:Ethylene: Water vapor 6.8:92.2:1 | 150 | 5 | 10.7 | 87.4 | 86.3 |
| Comp. Ex. 15 | Phosphotungstic acid | 10 | Acetic acid:Ethylene: Water vapor 6.8:92.2:1 | 150 | 5 | 10.7 | 86.1 | 84.6 |

We claim:

1. A process for the preparation of a lower fatty acid ester wherein a lower fatty acid is reacted with a lower olefin in gaseous phase by using as a solid catalyst at least one heteropoly-acid salt selected from cesium, rubidium, thallium, ammonium, potassium, barium, gold, sodium, lithium, copper and magnesium salts of phosphotungstic acid, silicotungstic acid, phosphomolybdic acid and silicomolybdic acid.

2. A process according to claim 1, wherein the lower fatty acid is selected from formic acid, acetic acid, propionic acid, valeric acid, acrylic acid, methacrylic acid, and crotonic acid.

3. A process according to claim 1, wherein the lower olefin is selected from ethylene, propylene, butene-1, butene-2, and isobutylene.

4. A process according to claim 1, wherein the lower fatty acid is acetic acid or acrylic acid, the lower olefin is ethylene, and the lower fatty acid ester is ethyl acetate or ethyl acrylate.

5. A process according to claim 1, wherein the reaction temperature is 50 to 300° C., and the reaction pressure is 0 to 50 kg/cm²G.

6. A process according to claim 1, wherein the reaction is carried out in the presence of water vapor.

7. A process according to claim 1, wherein the heteropoly-acid salt is supported on a carrier.

8. A process according to claim 7, wherein the carrier is selected from silica, diatomaceous earth, titania, activated carbon, alumina and silica-alumina.

9. A process according to claim 7, wherein the heteropoly-acid salt is supported on a carrier by coating, impregnation, evaporation to dry or kneading and molding.

10. A process for the preparation of a lower fatty acid ester wherein a lower fatty acid is reacted with a lower olefin in gaseous phase by using as a solid catalyst at least one member selected from heteropoly-acids and their salts represented by the general formula,

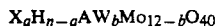

$$X_a H_{n-a} A W_b Mo_{12-b} O_{40}$$

wherein H, W, Mo, and O respectively represent hydrogen, tungsten, molybdenum, and oxygen, X represents at least one element or atomic group selected from the group consisting of potassium, rubidium, thallium, cesium, and ammonium, A represents at least one element selected from the group consisting of phosphorous and silicon, a represents an atomic ratio or molecular ratio of the elements or atomic groups, b is an integer of less than 12, not including 0, n is 3 when A is phosphorous, and n is 4 when A is silicon.

11. A process according to claim 10, wherein the lower fatty acid is selected from formic acid, acetic acid, propionic acid, valeric acid, acrylic acid, methacrylic acid, and crotonic acid.

12. A process according to claim 10, wherein the lower olefin is selected from ethylene, propylene, butene-1, butene-2, and isobutylene.

13. A process according to claim 10, wherein the lower fatty acid is acetic acid or acrylic acid, the lower olefin is ethylene, and the lower fatty acid ester is ethyl acetate or ethyl acrylate.

14. A process according to claim 10, wherein the reaction temperature is 50 to 300° C., and the reaction pressure is 0 to 50 kg/cm²G.

15. A process according to claim 10, wherein the reaction is carried out in the presence of water vapor.

16. A process according to claim 10, wherein the heteropoly-acid or its salt is selected from phosphotungstomolybdic acid, silicotungstomolybdic acid, and potassium, rubidium, thallium, cesium and ammonium salts or phosphotungstomolybdic acid or silicotungstomolybdic acid.

17. A process according to claim 10, wherein the heteropoly-acid or its salt is supported on a carrier.

18. A process according to claim 17, wherein the carrier is selected from silica, diatomaceous earth, titania, activated carbon, alumina and silica-alumina.

19. A process according to claim 17, wherein the heteropoly-acid or its salt is supported on a carrier by coating, impregnation, evaporation to dry or kneading and molding.

* * * * *